(12) United States Patent
Nashman et al.

(10) Patent No.: US 11,931,137 B2
(45) Date of Patent: *Mar. 19, 2024

(54) WEAK SIGNAL DETECTION SYSTEM AND METHOD

(71) Applicant: Synex Medical Inc., Toronto (CA)

(72) Inventors: Benjamin Saul Nashman, Toronto (CA); Sean Kentaro Sullivan Takahashi, Toronto (CA); Abenezer Teklemariam, Toronto (CA)

(73) Assignee: Synex Medical Inc., Toronto (CA)

( * ) Notice: Subject to any disclaimer, the term of this patent is extended or adjusted under 35 U.S.C. 154(b) by 146 days.

This patent is subject to a terminal disclaimer.

(21) Appl. No.: 17/711,815

(22) Filed: Apr. 1, 2022

(65) Prior Publication Data

US 2022/0273186 A1 Sep. 1, 2022

Related U.S. Application Data

(63) Continuation of application No. 17/388,264, filed on Jul. 29, 2021, now Pat. No. 11,317,822.

(60) Provisional application No. 63/148,847, filed on Feb. 12, 2021, provisional application No. 63/059,525, filed on Jul. 31, 2020.

(51) Int. Cl.
  *A61B 5/00* (2006.01)
  *A61B 5/055* (2006.01)

(52) U.S. Cl.
  CPC .......... *A61B 5/055* (2013.01); *A61B 5/0024* (2013.01); *A61B 5/7257* (2013.01)

(58) Field of Classification Search
  CPC ..... A61B 5/055; A61B 5/0024; A61B 5/7257; A61B 5/14532; A61B 5/14546; A61B 5/7203
  See application file for complete search history.

(56) References Cited

U.S. PATENT DOCUMENTS

| | | | |
|---|---|---|---|
| 6,577,888 B1 * | 6/2003 | Chan | G01R 33/3415 324/318 |
| 6,865,494 B2 * | 3/2005 | Duensing | G01R 33/44 324/722 |
| 7,084,626 B2 * | 8/2006 | Ma | G01R 33/5611 324/309 |
| 7,405,567 B2 | 7/2008 | McDowell | |
| 7,734,324 B2 * | 6/2010 | Biglieri | A61B 8/5238 600/407 |
| 8,560,034 B1 * | 10/2013 | Diab | A61B 5/14551 600/323 |
| 9,285,441 B1 | 3/2016 | McDowell | |

(Continued)

FOREIGN PATENT DOCUMENTS

CN 104898172 B 5/2017

*Primary Examiner* — May A Abouelela
(74) *Attorney, Agent, or Firm* — Jeffrey Schox; Diana Lin

(57) ABSTRACT

In variants, a method for signal enhancement includes: sampling a set of measurements of a signal source; and determining a SNR-enhanced signal based on the measurements, which, in variants, can include recursively cross-correlating elements for d iterations S200; and determining a SNR-enhanced signal from the cross-correlation outputs. The method functions to determine a SNR-enhanced signal representative of the signal source. The method can optionally include determining an analyte parameter based on the SNR-enhanced signal.

20 Claims, 15 Drawing Sheets

(56) References Cited

U.S. PATENT DOCUMENTS

| | | | |
|---|---|---|---|
| 10,444,311 B2* | 10/2019 | Wang | A61B 5/004 |
| 10,739,428 B2 | 8/2020 | McDowell | |
| 10,768,255 B2* | 9/2020 | Rothberg | G01R 33/385 |
| 10,845,441 B1 | 11/2020 | McDowell | |
| 11,204,405 B1 | 12/2021 | McDowell | |
| 2006/0264738 A1* | 11/2006 | Hashimshony | A61B 5/055 |
| | | | 600/410 |
| 2010/0081918 A1* | 4/2010 | Sugiura | A61B 5/055 |
| | | | 600/410 |
| 2010/0141256 A1 | 6/2010 | Feng | |
| 2011/0009732 A1* | 1/2011 | Sugiyama | G06T 7/0016 |
| | | | 600/410 |
| 2014/0011217 A1 | 1/2014 | Weissleder et al. | |
| 2015/0257675 A1* | 9/2015 | Bottomley | G01R 33/4818 |
| | | | 600/423 |
| 2016/0025835 A1* | 1/2016 | Gulani | G01R 33/5635 |
| | | | 600/420 |
| 2016/0120438 A1* | 5/2016 | Cima | A61B 5/6826 |
| | | | 600/410 |
| 2018/0143274 A1* | 5/2018 | Poole | A61B 6/4405 |
| 2018/0224512 A1* | 8/2018 | Poole | G01R 33/36 |
| 2019/0041476 A1* | 2/2019 | Otake | G01R 33/343 |
| 2020/0258199 A1* | 8/2020 | Shirai | G01R 33/4835 |
| 2020/0294287 A1* | 9/2020 | Schlemper | G06T 7/0012 |
| 2021/0116523 A1* | 4/2021 | Yatsuo | G01R 33/3621 |

* cited by examiner

| Number of initial data sets | $d$-cross correlations | Number of uniquely defined $d$-cross correlations ($C$) |
|---|---|---|
| 2 | 1 | 1 |
| 4 | 2 | 3 |
| 8 | 3 | 315 |
| 16 | 4 | 638 576 875 |
| 32 | 5 | $\sim 1.225 \times 10^{26}$ |

FIGURE 14

| Number of Signals ($m$) | $\sum_{n=1}^{m-1} n$ | Cross correlation steps ($m-1$) |
|---|---|---|
| 4 | 6 | 3 |
| 8 | 21 | 7 |
| 16 | 105 | 15 |
| 64 | 2016 | 63 |

WEAK SIGNAL DETECTION SYSTEM AND METHOD

CROSS-REFERENCE TO RELATED APPLICATIONS

This application is a continuation of U.S. application Ser. No. 17/388,264 filed 29 Jul. 2021, which claims the benefit of U.S. Provisional Application No. 63/059,525 filed 31 Jul. 2020 and U.S. Provisional Application No. 63/148,847 filed 12 Feb. 2021, each of which is incorporated in its entirety by this reference.

TECHNICAL FIELD

This invention relates generally to the magnetic resonance field, and more specifically to a new and useful method for signal-to-noise enhancement in the nuclear magnetic resonance field.

BACKGROUND

Magnetic resonance (MR) measurements, particularly nuclear magnetic resonance (NMR) measurements, are inherently insensitive because they measure very small energy differences in nuclear spin states. This results in a very weak signal that is easily overpowered by noise from the sampling environment and equipment.

In biological environments, this results in an even weaker signal, because the molecules of interest (e.g., analytes) are present in relatively low concentrations in the body. The signal can be further weakened or overpowered when low magnetic field strengths are used.

Conventionally, MR systems run and process (e.g., average, sum) multiple scans to amplify a signal (e.g., N measurements to obtain a $\sqrt{N}$ improvement in SNR. Unfortunately, the high number of scans required to obtain this improvement is prohibitive to continuous NMR monitoring, because NMR's coherence timelines are extremely long (e.g., up to 10 seconds for proton in ambient conditions). By the time a sufficient number of scans have been recorded, the underlying analyte concentration, biological context, and/or magnetic environment would have changed.

Thus, there is a need in the magnetic resonance field to create a new and useful system and method for NMR signal enhancement.

BRIEF DESCRIPTION OF THE FIGURES

FIG. 14 is an example of the number of uniquely defined d-cross-correlations for a given combination of initial data sets (m) and number of cross-correlation iterations (d).

DETAILED DESCRIPTION

The following description of the preferred embodiments of the invention is not intended to limit the invention to these preferred embodiments, but rather to enable any person skilled in the art to make and use this invention.

1. Overview

Figure 1:
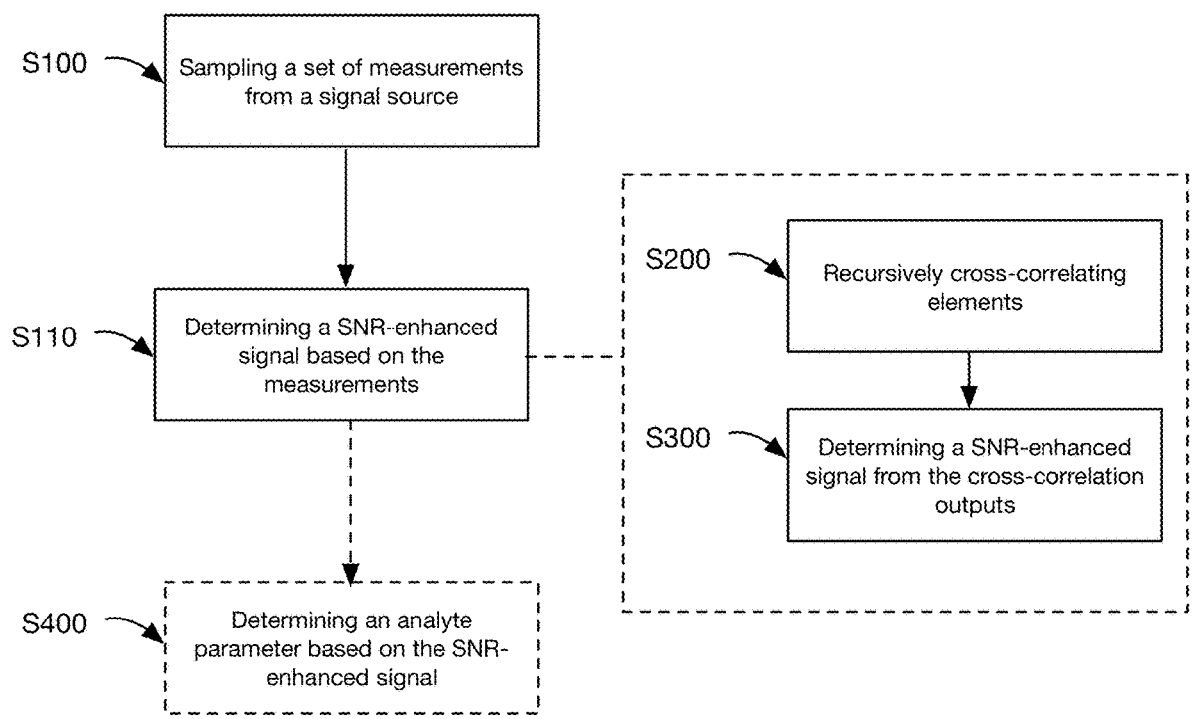
FIG. 1 is a flowchart diagram of the method.

As shown in FIG. 1, the method for signal enhancement includes: sampling a set of measurements of a signal source S100; and determining a SNR-enhanced signal based on the measurements S110. In variants, S110 can include recursively cross-correlating elements S200; and determining a SNR-enhanced signal from the cross-correlation outputs S300. The method functions to determine a SNR-enhanced signal representative of the signal source. The method can optionally include determining an analyte parameter based on the SNR-enhanced signal S400.

In an example, the method recursively cross-correlates signal measurements to amplify a weak signal for detection (REcursive Cross-CoRrelation for WEak SignAl DeTEction, or RECREATE). In this example, the method includes: sampling m measurements of a signal source (e.g., m free induction decay (FID) measurements); recursively cross-correlating the m measurements for d recursion loops (e.g., in the time or frequency domain), wherein the output of the prior loop is used as the input for the subsequent loop, wherein the $d^{th}$ iteration outputs N unique cross correlation outputs; summing the N unique cross-correlation outputs to generate a SNR-enhanced signal (e.g., signal representative of the signal source, in the time or frequency domain); optionally processing the SNR-enhanced signal (e.g., zero-filling, line broadening, phase correction, baseline correction, etc.); transforming the SNR-enhanced signal into the frequency domain (e.g., using a Fourier transform); and calculating an analyte parameter (e.g., concentration, mass, etc.) based on the SNR-enhanced signal.

2. Benefits.

This system and method can confer several benefits over conventional systems and methods.

First, the system and method can obtain a SNR improvement by cross-correlating the measurements (e.g., as compared to the original measurement, as compared to simply summing the measurements). The system and method can further obtain a $\sqrt{N}$ improvement using less than N measurements. The inventors have discovered that the signal can be enhanced not only by cross-correlating the signal measurements, but that the cross-correlation results can be further cross-correlated (e.g., recursively cross-correlated) to generate N cross-correlation outputs. These N cross-correlation outputs can then be used to determine the analyte signal (e.g., because the cross-correlated results are exponentials with the same functional form as the original NMR measurements in lag space, with the correct frequencies and correct decay constants), resulting in a highly denoised signal that preserves the same functional form as original pure source signal with $\sqrt{N}$ signal improvement.

Second, by manipulating the signal measurements in the time domain, this method can preserve the spectra in the frequency domain and/or enhance the spectra (e.g., enhance larger amplitude signals, line broadening, etc.), which preserves or enhances the analyte information embedded in the signal measurement. This can allow for the system and method to function as an ideal filter in the frequency domain. This is because the time-domain signal is a damped exponential for an FID, and because, according to the Cross-Correlation Theorem, the Fourier transform of the cross-correlation of two continuous functions is equivalent to its cross power spectral density, so the cross-correlation must retain the information. For two equivalent functions, such as two equivalent free induction decay signals, this is described by the Wiener-Khinchin Theorem, where the cross-correlation can be said to be an autocorrelation, whose Fourier transform is the power spectrum of the function. Furthermore, cross-correlation in the time domain can be better than cross-correlation in the frequency domain, since the time domain is less sparse than the frequency domain in high-resolution MRS, and thus has more non-zero, true signal amplitude points to correlate; however, cross-correlation can alternatively be performed in the frequency domain and/or any other suitable domain.

Third, by achieving a $\sqrt{N}$ improvement using less than N measurements, the system and method can decrease the sampling time, which can confer a better user experience. This shortened sampling time can be particularly desirable when the measurements are sampled from a human or user, who may be unable to hold still for extended measurement periods. The system and method can also decrease the requisite coil sensitivity, thereby lowering system cost and/or enabling easier manufacturing. The system and method can also decrease the amount of memory and processing power used, since less samples need to be stored and processed.

However, the system and method can confer any other suitable set of benefits.

3. System.

The system for weak signal detection can include a processing system connected to a measurement system.

The processing system can be collocated with a measurement system (e.g., onboard or located nearby the measurement system), remote from the measurement system (e.g., be a remote computing system, a cloud computing system, etc.), or otherwise located. The processing system can include one or more of: a CPU, GPU, microprocessor, TPU, a server system (e.g., on-premises system, cloud computing system, etc.), distributed computing system, a user device's processing system, a combination thereof, and/or any other suitable processing system. The processing system can be connected to the measurement system by a wired connection, wireless connection (e.g., WiFi, Internet, Bluetooth, NFC, etc.), and/or any other suitable connection.

The measurement system can sample measurements of one or more signal sources, wherein the measurements are processed by the processing system.

The measurements are preferably indicative of a parameter of the signal source, examples of which are provided below. The measurements can be measurements of nuclear magnetic resonance response, electromagnetic signals (e.g., radiofrequency signals), optical signals, acoustic signals, and/or other signals. The measurements can be in the time domain, the frequency domain, and/or in any other suitable domain. The measured signals can be damped exponential signals, decaying sinusoidal signals, periodic signals, arbitrary signals, and/or have any other characteristic. The measurements can be NMR signals (e.g., FID signals), MR signals, and/or any other suitable set of signals. The measurements can be noisy. The noise is preferably uncorrelated (e.g., uncorrelated with another measurement of the same sample), but can be correlated. The noise can be: random noise, Gaussian noise, white noise, black noise, pink noise, Brownian noise, Cauchy noise, Poisson noise, and/or other types of noise. The measurement system can concurrently sample one or more measurements, or sample the measurements sequentially.

The signal source (e.g., analysis target) is preferably an analyte within an analysis sample, but can be another signal source (e.g., repeatable signal source). The analytes can be: proteins, amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, pyrrolysine, selenocysteine, aspartic acid or asparagine, glutamic acid or glutamine, leucine or isoleucine, etc.), nucleic acids (e.g., DNA, RNA, etc.), nucleotides (e.g., guanine, adenine, cytosine, thymine, etc.), biomarkers (e.g., glucose, lactate, alanine, hormones, disease markers, metabolites, molecular biomarkers, cellular biomarkers, imaging biomarkers, etc.), and/or other molecules of interest.

Figure 4:
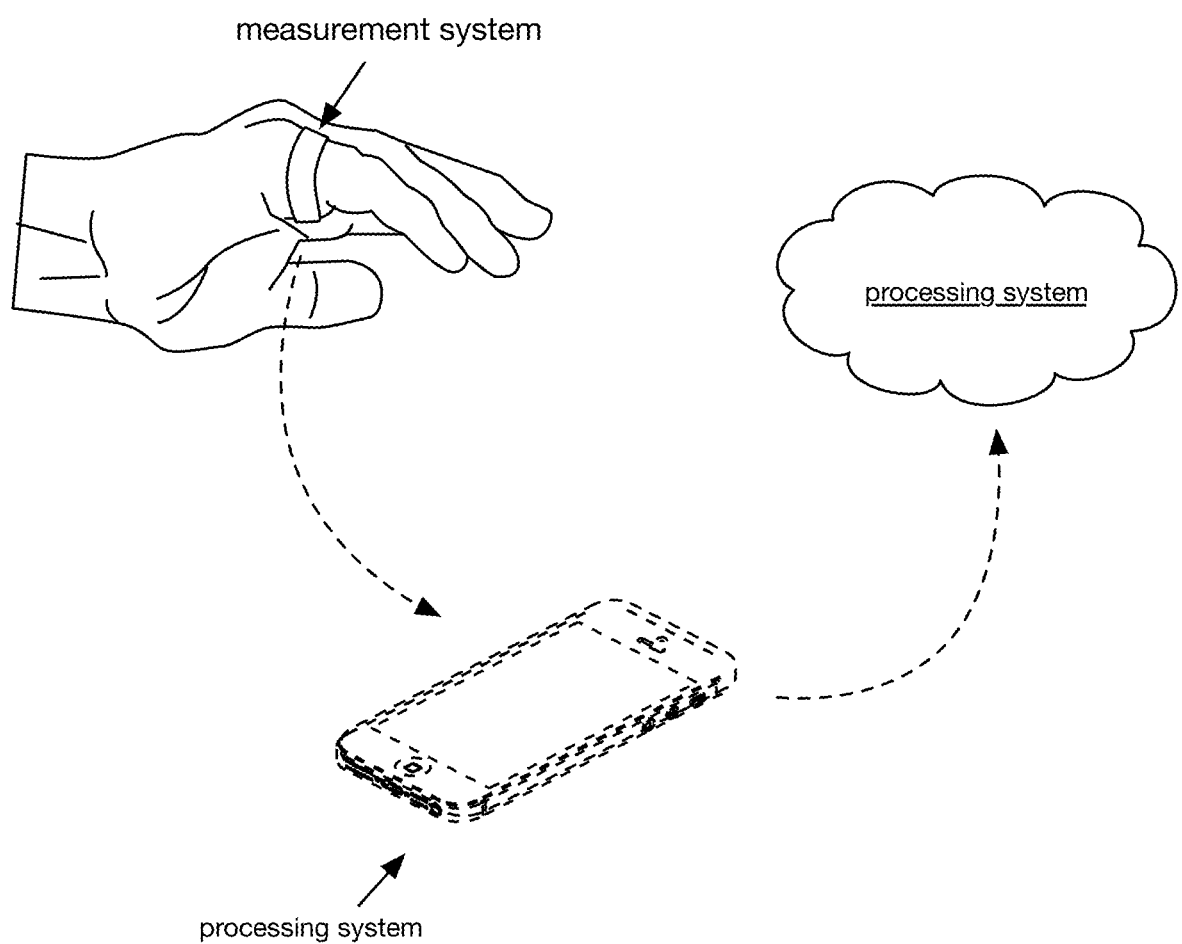
FIG. 4 is a schematic representation of a variant of a system for signal enhancement.

The analysis sample is preferably a biological sample, but can alternatively be a nonbiological sample, or have another composition. The biological sample is preferably in-vivo, such that the unique measurements are in-vivo measurements (e.g., measurements of the analyte in a subject's blood), but can alternatively be in-vitro or otherwise arranged relative to a subject (e.g., user, animal, etc.). The sampled biological sample is preferably less than a predetermined volume (e.g., less than 400 mm$^2$, less than 500 cm$^2$, etc.), but can alternatively be larger. The analysis sample is preferably an animal body part (e.g., human body part, nonhuman body part, etc.), but can alternatively be a sample tube (e.g., beaker), an uncontained solution, and/or any other suitable sample. The animal body part can be an extremity, such as an finger (example shown in FIG. 4), wrist, arm, toe, ankle, leg, or neck; be a torso; and/or be another body part (e.g., of a user).

The measurement system can sample one or more measurements: contemporaneously (e.g., concurrently, during overlapping time windows, etc.), sequentially (e.g., serially, asynchronously, etc.), and/or at any other suitable time. The measurement system can contemporaneously or sequentially sample measurements for a single signal source, multiple signal sources, and/or any other suitable number of signal sources. The measurement system can contemporaneously or sequentially sample measurements from a single analysis sample, multiple analysis samples, and/or any other suitable number of analysis samples.

The measurement system can include one or more: housings, magnetic elements (e.g., permanent magnets), emitters, sensors, and/or other components. All or a portion of the measurement system components can be located within and/or mounted to the housing, or be remote or outside of the housing.

The housing functions to define a measurement volume configured to receive the analysis sample, to retain and protect the system components, and/or perform other functionalities. The housing can define a desktop system, define a non-desktop system, define a ring, define a bracelet, define a necklace, and/or define any other suitable form factor. The measurement volume can be: a bore, a cavity (e.g., with one or more closed ends), a lumen, and/or any other suitable volume. The measurement volume can be dimensioned to receive and/or retain an analysis sample, or be otherwise dimensioned. For example, the measurement volume diameter can be smaller than 50 mm, smaller than 30 mm, between 14 mm-25 mm, larger then 10 mm, and/or have any other suitable size.

The magnetic elements function to apply a magnetic field. The magnetic elements are preferably arranged about the measurement volume (e.g., above, below, encircle, within, etc.) to induce a magnetic field having a predetermined set of magnetic field parameters (e.g., strength, gradient, etc.) within the measurement volume, but can be otherwise arranged. Examples of magnetic elements that can be used include: permanent magnets, electromagnets (e.g., coils), shims, ferrous elements, and/or any other suitable element. The applied magnetic field preferably has a low field strength (e.g., less than 2 T, less than 1 T, less than 0.5 T, less than 0.1 T, etc.), but can alternatively have any other suitable field strength (e.g., more than 2 T, more than 5 T, more than 10 T, more than 20 T, between 0.01-20 T, etc.).

The emitters function to apply an excitation signal to the analysis sample within the measurement volume. The excitation signal can be: a radiofrequency (RF) pulse, an optical pulse, an acoustic pulse, an electrical pulse, and/or any other suitable signal. The excitation signal is preferably a sequence (e.g., pulse sequence), but can alternatively be a single pulse. The excitation signal is preferably tailored to the signal source, but can alternatively be tailored toward the solvent, other solutes, and/or other molecules. For example, the excitation signal can be an RF signal the is close to the Larmor frequency of the nuclear spins of the signal source. In this example, the emitter and/or sensor can optionally include or be connected to an RF processor (e.g., RF module) that generates and/or processes the RF pulse. However, the excitation signal can be otherwise constructed. The emitters can be: antennas, transmitters, lights, speakers, electrodes, and/or any other suitable emitter. The measurement system can include a single emitter for each sensor, a single emitter for multiple sensors, multiple emitters for a single sensor, and/or any other suitable ratio of emitters to sensors. The emitters are preferably decoupled (e.g., electrically, acoustically, optically, etc.) from the sensors and/or each other, but can alternatively be coupled. The emitters are preferably arranged about the measurement volume (e.g., above, below, encircle, within, etc.) to apply an excitation signal to an analysis sample within the measurement volume, but can be otherwise arranged.

The sensors function to sample measurements of a signal or response generated (e.g., emitted) by the signal source after excitation. The measurements can be an NMR signal (e.g., free induction decay (FID)), MR signal, an image, an audio stream, a voltage, a current, and/or any other suitable measurement. The sensors can be coils, receivers, cameras, microphones, electrodes, and/or any other suitable sensors. The sensors are preferably decoupled (e.g., electrically, acoustically, optically, etc.) from the emitters and/or each other, but can alternatively be coupled. The sensors are preferably arranged about the measurement volume (e.g., above, below, encircle, within, etc.) to measure the signal from the measurement volume, but can be otherwise arranged.

Figure 5:
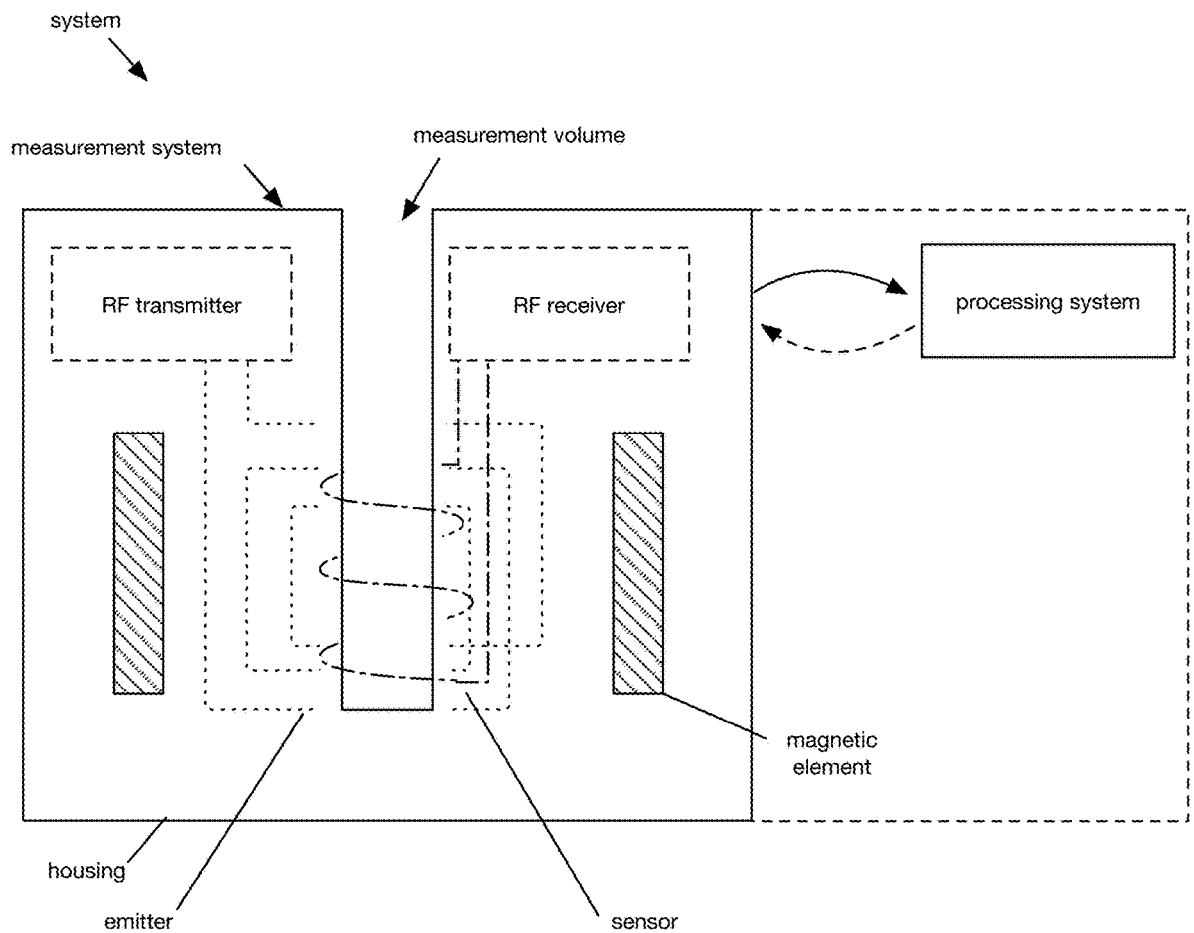
FIG. 5 is a schematic representation of an illustrative example of a system for signal enhancement.

In one example (illustrative example shown in FIG. 5), the measurement system can include: a housing defining a measurement volume, a set of magnetic elements arranged to induce a predetermined magnetic field within the measurement volume, a set of coils (e.g., receivers, NMR coils, etc.) arranged about the measurement volume and configured to sample measurements (e.g., signals) from the measurement volume, a set of RF antennae (e.g., coils, transmitters) arranged about the measurement volume and configured to apply an RF pulse to the measurement volume, a processing system configured to process the measurements, and/or other components.

Examples of measurement systems that can be used include: an NMR measurement system, an NMR spectrometer (e.g., low-field NMR spectrometer), the system described in U.S. application Ser. No. 16/762,010 filed 6 May 2020, incorporated herein in its entirety by this reference, other magnetic resonance measurement systems, a user device (e.g., smartphone, tablet, smartwatch, etc.), or other measurement systems. In a specific example, S100 is performed using a low-field NMR spectrometer at room or body temperature.

However, any other suitable system can be used.

4. Method.

As shown in FIG. 1, the method for signal enhancement includes: sampling a set of measurements of a signal source S100; and determining a SNR-enhanced signal based on the measurements S110. In variants, S110 can include recursively cross-correlating elements S200; and determining a SNR-enhanced signal from the cross-correlation outputs S300.

The method is preferably performed by the system discussed above, more preferably by the processing system (example shown in FIG. 4) but additionally or alternatively the measurement system, or be performed by any other suitable system.

The method is preferably performed periodically (e.g., at a predetermined frequency), but can alternatively be performed in response to occurrence of an analysis event (e.g., user request receipt, device request receipt, time expiration, etc.) or at any other time. A different method instance is preferably performed for each individual sample source (e.g., analyte), but a single method instance can alternatively be performed for multiple sample sources.

Sampling a set of measurements S100 functions to sample one or more measurements from the one or more signal sources.

The signal measurements are preferably the observed free induction decay (FID) of the analyte after excitation, but can be any other suitable measurement. Each signal measurement can include multiple data points (e.g., representing a response for a point in time). The number data points is preferably a power of 2, but can be any suitable number.

The signal measurements within the set are preferably measurements of an analysis sample, but can additionally or alternatively be known measurements, such as reference measurements or synthetic measurements (e.g., wherein the set can include or exclude known measurements or signals), and/or be any other suitable measurement. The reference measurement can be generated from a reference sample (e.g., separate from the analysis sample), wherein the reference sample can have known or controlled parameters, such as known signal source parameters (e.g., known analyte concentration, identity, mass, etc.), known noise, and/or other parameters. However, another reference sample can be used.

Each signal measurement is preferably sampled at a sampling frequency, wherein each sample can generate a data point of the overall measurement. The sampling frequency can: be predetermined; be selected based on: the pulse parameters (e.g., pulse strength, pulse pattern, etc.), the analyte of interest, the measurement system configuration, the analyte's relaxation time, a multiple (e.g., 2), an acquisition time, a minimum number of samples needed for the analysis, the available computing resources, and/or other operation parameters; be a maximum frequency permitted by the measurement system; and/or otherwise determined. Different measurements within the set can be sampled at the same or different sampling frequency.

Each signal measurement is preferably acquired over the duration of an acquisition time (e.g., sampling time window). The acquisition time can be: predetermined (e.g., 1 second, 5 seconds, 10 seconds, 1 minute, 10 minutes, 1 hour, shorter than 1 second, longer than 1 hour, a duration between 1 second and 1 hour, etc.), determined based on the analyte of interest (e.g., based on the relaxation time, based on the analyte's half life within the analysis sample), determined based on the SNR of the measurement, or the coil (e.g., determined from a prior measurement), determined based on the frequency resolution, determined based on the spectral width, defined by user parameters or preferences (e.g., calculated, using a lookup table, etc.; where children can have shorter sampling time windows than adults; etc.), determined based on a maximum acquisition duration (e.g., the maximum amount of time that all m measurements must be sampled within, such as 1 minute, 5 minutes, 10 minutes, 30 minutes, an hour, a duration between 1 second and 1 hour, longer than an hour, less than 1 minute, etc.), and/or otherwise determined. The acquisition time can be calculated, manually selected, optimized (e.g., balancing high frequency resolution versus the number of data points), and/or otherwise determined. Different measurements within the set can be sampled using the same or different acquisition time.

Each signal measurement is preferably acquired using an excitation signal. The excitation signal is preferably an RF signal that is close to the Larmor frequency of the nuclear spins of the signal source, but can alternatively be any other suitable signal. The excitation signal preferably includes a pulse sequence (e.g., tailored to the signal source), but can alternatively include a single pulse. Different measurements within the set can be sampled using the same or different excitation signal instance. Different measurements within the set can be sampled using the same or different excitation signal (e.g., the same or different RF pulse sequence).

The set of measurements preferably includes m signal measurements of a given signal source (e.g., shared signal source), where m is preferably more than two signal measurements, but can alternatively be less (e.g., 1). m can be: predetermined (e.g., 2, 4, 8, 16, 32, be a power of two, such as $2^d$, etc.), calculated from d (e.g., determined in S210), be dictated by hardware, the relaxation time, analyte concentration, user preferences, acquisition time, and/or otherwise determined.

Different measurements within the set can be generated from the same excitation (e.g., from the same pulse) or different excitations. In the latter variant, the excitation parameters of the different excitations (e.g., amplitude, applied energy, excitation pattern, etc.) are preferably the same for different measurements, but can alternatively be different. Different measurements within the set can be sampled by the same or different receiver.

Different measurements within the set are preferably sampled from the same signal source, but can alternatively be sampled from different sample sources. Different measurements within the set are preferably sampled from the same analysis sample, but can alternatively be sampled from different analysis samples.

Different measurements in the set can be sampled: contemporaneously (e.g., concurrently, during overlapping windows, etc.), serially, and/or with any other suitable temporal relationship. For example, multiple measurements for the same analyte from the same sample can be measured: concurrently, serially, or at any time. Measurements for different analytes from the same sample can be measured: concurrently, serially, during overlapping periods, or at any time.

The signal measurements within the set are preferably unique, but can alternatively be nonunique. For example, the unique signal measurements can be: sampled by different receiver channels (e.g., independent, decoupled receiver channels), sampled at different times (e.g., different acquisition periods, different sampling epochs, different timestamps, etc.), sampled from different excitations, sampled using a combination of the above, uncorrelated with other measurements within the set, include noise that is uncorrelated with the noise of other measurements within the set, or otherwise differentiated. The signal measurements of the set are preferably in phase (e.g., $\phi=0$), but can be out of phase relative to each other.

S100 can include: applying a magnetic field to the analysis sample with a measurement system, exciting the analyte with an RF pulse (e.g., with a pulse pattern and/or other pulse parameters tuned for the signal source), and measuring the analyte's nuclear magnetic resonance response as the signal measurement (e.g., the free induction decay (FID)). S100 can optionally include receiving the analysis sample (e.g., within the measurement volume or measurement system) before magnetic field application and/or analyte excitation. However, S100 can be otherwise performed.

In a first variation, the measurement system includes a plurality of coils, wherein S100 includes: applying a magnetic field to the analysis sample (e.g., located within the measurement volume); exciting the analyte with an RF pulse (e.g., tuned for the analyte); and sampling the response at each of the plurality of coils, wherein the measurement from each coil cooperatively form the measurement set.

In a second variation, the measurement system includes a plurality of coils, wherein S100 includes: applying a magnetic field to the analysis sample (e.g., located within the measurement volume); exciting the analyte with a set of RF pulses, each having a different phase; and sampling the responses at each of the plurality of coils, wherein the measurement from each coil cooperatively form the measurement set. Each coil can sample the responses from all, a subset, or a single phase.

In a third variation, the measurement system includes a single coil (e.g., for the analyte), wherein S100 includes: applying a magnetic field to the analysis sample (e.g., located within the measurement volume); and iteratively: exciting the analyte with an RF pulse (e.g., after the analyte's relaxation time) and sampling the response with the coil. The sequentially-generated measurements can cooperatively form the measurement set.

However, the signals can be otherwise measured.

The signal measurements can be independently sampled (e.g., by iteratively performing S100), extracted from a single sample, or otherwise sampled.

In a first variation, S100 is repeated at least m times to sample m signal measurements.

Figure 6:
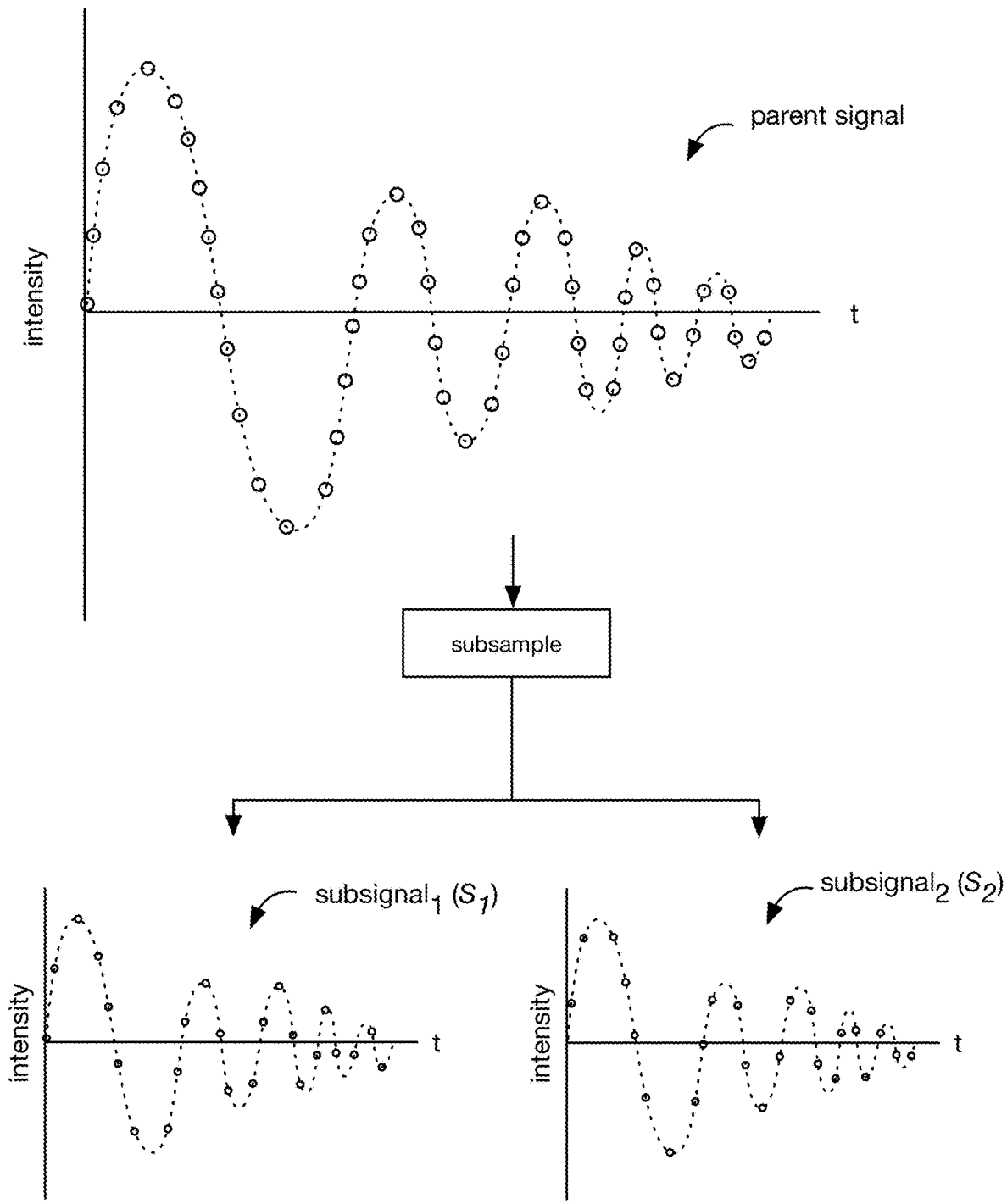
FIG. 6 is an illustrative example of subsampling an oversampled parent signal.

In a second variation, a single signal measurement (parent signal) is sampled, and at least m subsignals are then subsampled from the single signal measurement (example shown in FIG. 6). This variant can substantially shorten the acquisition time, since a single signal measurement is required instead of m signal measurements. The parent signal is preferably oversampled (e.g., sampled at a higher frequency than desired, etc.), but can alternatively be undersampled or sampled at any other suitable frequency. The parent signal is preferably sampled at a frequency of at least m*f, where m is the number of subsignals and f is the subsignal frequency, but can alternatively be sampled at a hardware-specified frequency (e.g., wherein the subsignal frequency f is $$\frac{1}{m} * \text{parent frequency}),$$

and/or be sampled at any other suitable frequency.

The subsignals are preferably downsampled versions of the parent signal, and can be randomly sampled, uniformly sampled, sampled at predetermined intervals, or otherwise sampled from the parent signal, or be otherwise related to the parent signal. The subsignals are preferably interleaved with each other (e.g., represent multiple parts of the parent signal), but can be otherwise related to each other or to the parent signal. The subsignals preferably do not share the same datapoints (e.g., do not overlap), but can alternatively share datapoints. The noise between the subsignals are preferably uncorrelated, but can alternatively be correlated. The subsignals preferably have the same sampling frequency f (e.g., are evenly sampled from the parent signal; are subsampled at the same subsampling rate), but can alternatively have different sampling frequencies from each other. The subsignal sampling frequency f preferably exceeds the Nyquist rate, where the Nyquist rate is double the frequency of the analyte resonating at the highest frequency, but can alternatively be any other suitable frequency. However, the parent and/or subsignal sampling frequencies can be otherwise determined.

However, the unique signal measurements can be otherwise determined.

The method can optionally include processing the signal measurements. The processed measurements can be used in subsequent processes (e.g., S110, S200, S300, etc.) or otherwise used. Processing the signal measurements can include: filtering (e.g., removing high-frequency noise), anomalous point removal, data point sampling, signal compression, weighting, cropping, aligning (e.g., to other measurements), combination (e.g., summing different measurements, averaging different measurements, multiplying measurements, etc.), normalization, and/or other processing methods. Weighting the measurements can include: exponential weighting (e.g., to amplify and/or emphasize the beginning of the measured signal); weighting the signals based on the signal or coil's SNR (e.g., enhancing or upweighting signals with higher SNR, suppressing or downweighting signals with lower SNR, etc.); and/or otherwise weighting the signals.

Determining a SNR-enhanced signal based on the measurements S110 functions to combine the measurements within the measurement set to remove the uncorrelated noise from the measurements and/or amplify the analyte signal (e.g., shared across all unique measurements). S110 can be performed in the time domain, frequency domain, and/or any other suitable domain.

S110 preferably includes recursively cross-correlating elements S200 and determining the SNR-enhanced signal from the cross-correlation outputs S300. Alternatively, S110 can include autocorrelating the unique measurements with themselves (e.g., to amplify the analyte signal within each unique measurement), then combining (e.g., summing, averaging) the multiple autocorrelated unique measurements. Since the noise in the different unique measurements are uncorrelated, summing or averaging the autocorrelated unique measurements can subtract the noise from the result. However, S110 can additionally or alternatively include: summing the measurements (e.g., and optionally assuming the noises approximate a Gaussian distribution); averaging the measurements (e.g., in the time domain); filtering the measurements or a combination thereof (e.g., using adaptive filters); applying a convolution to the measurements (e.g., a single convolution, recursive convolutions in a similar manner to S200, etc.); and/or applying other noise removal methods or combinations thereof.

Recursively cross-correlating elements S200 functions to generate the N cross-correlation outputs, wherein each subsequent cross-correlation removes uncorrelated noise from the inputs (examples shown in FIGS. 10-13). The cross-correlated elements are preferably unique, but can alternatively be nonunique. The N cross-correlation outputs are preferably unique, but can alternatively be nonunique.

S200 is preferably performed by the processing system, but can be performed by another system. All or portions of S200 is preferably performed in the time domain, but can be performed in the frequency domain, in a dense or non-sparse domain of the signal (e.g., with data points denser than a threshold density), in a sparse domain of the signal (e.g., with data points sparser than a threshold density), in a multi-dimensional domain (e.g., for multi-dimensional measurements, such as 2D measurements or 3D measurements; multi-dimensional transforms, such as 2D transforms of 1D measurements, 3D transforms of 2D measurements; etc.), or otherwise performed. S200 can be performed after all measurements are sampled in S100, while S100 is being performed, and/or at any other suitable time.

Figure 2:
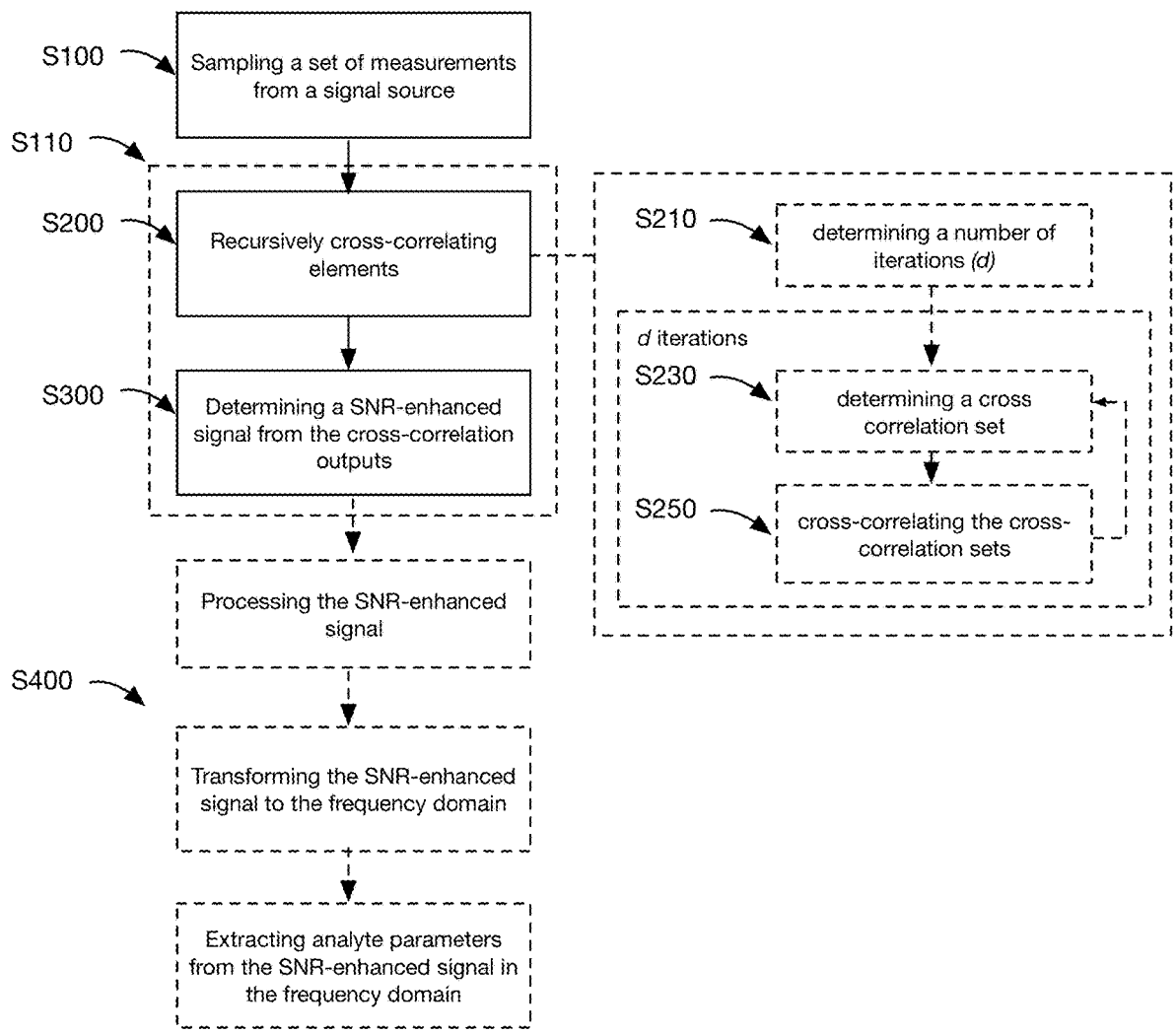
FIG. 2 is a flowchart diagram of an example of the method.
Figure 9:
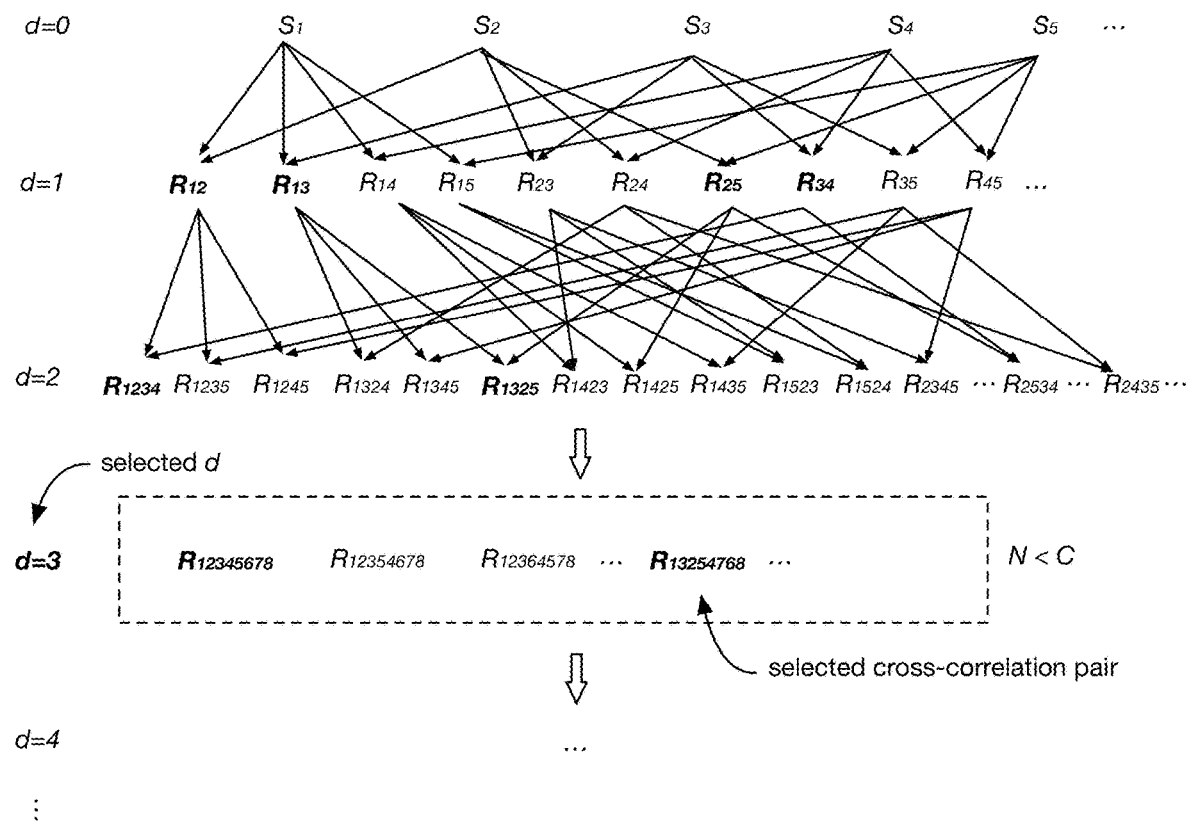
FIG. 9 is an illustrative example of selecting d and cross-correlation sets.
Figure 10:
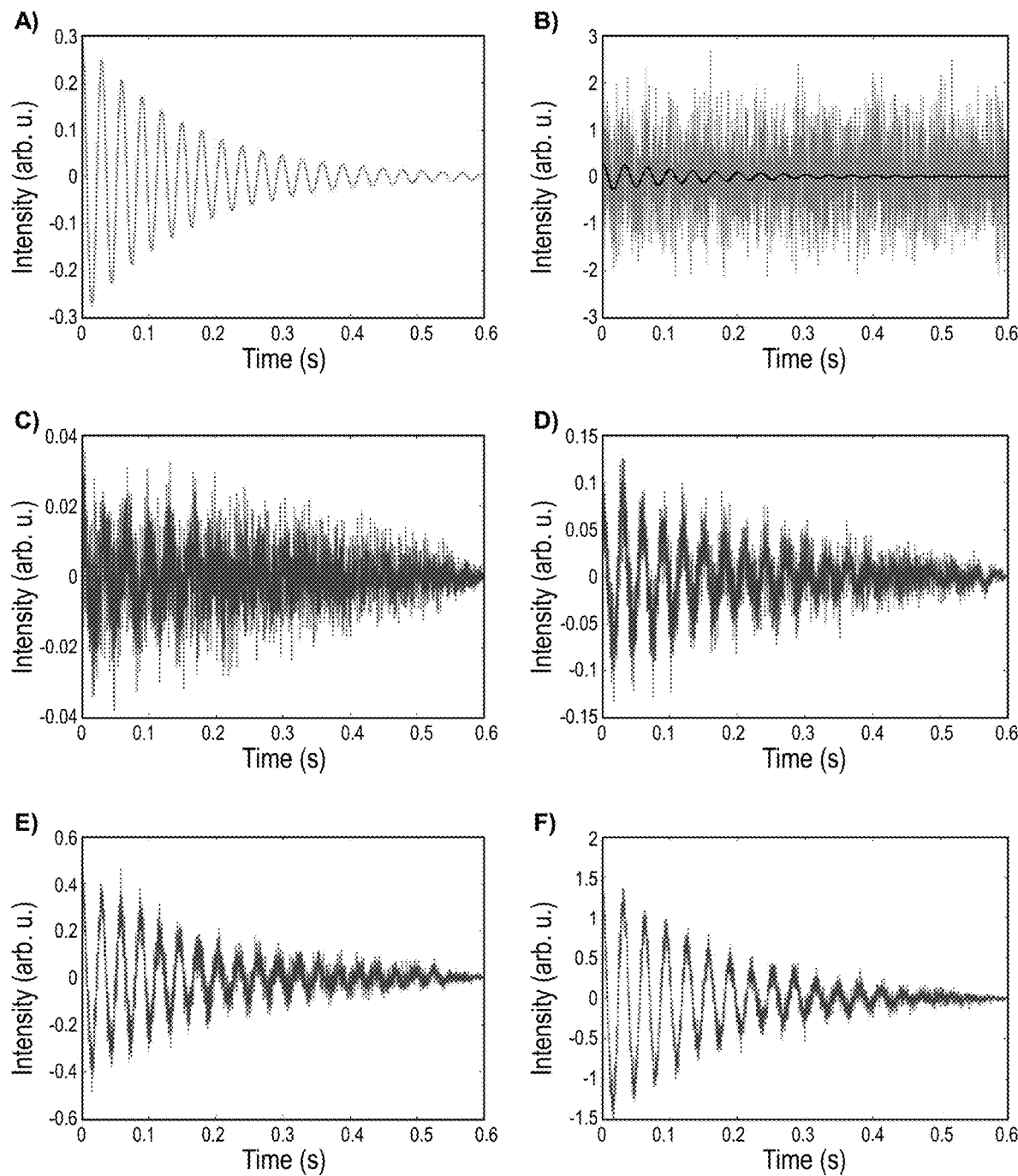
FIG. 10 is a first illustrative example of the method, depicting the effect of different numbers of initial FIDs with RECREATE using 1-cross-correlation. The initial SNR of the noisy signal is 0.3 and the number of data points per signal is 4096 A) The true FID without noise. B) The true signal with additive, white Gaussian noise with SNR=0.3. True signal overlaid in red to show scale. C) The recovered signal with 2 initial FIDs. D) The recovered signal with 4 initial FIDs. E) The recovered signal with 8 initial FIDs. F) The recovered signal with 16 initial FIDs.
Figure 11:
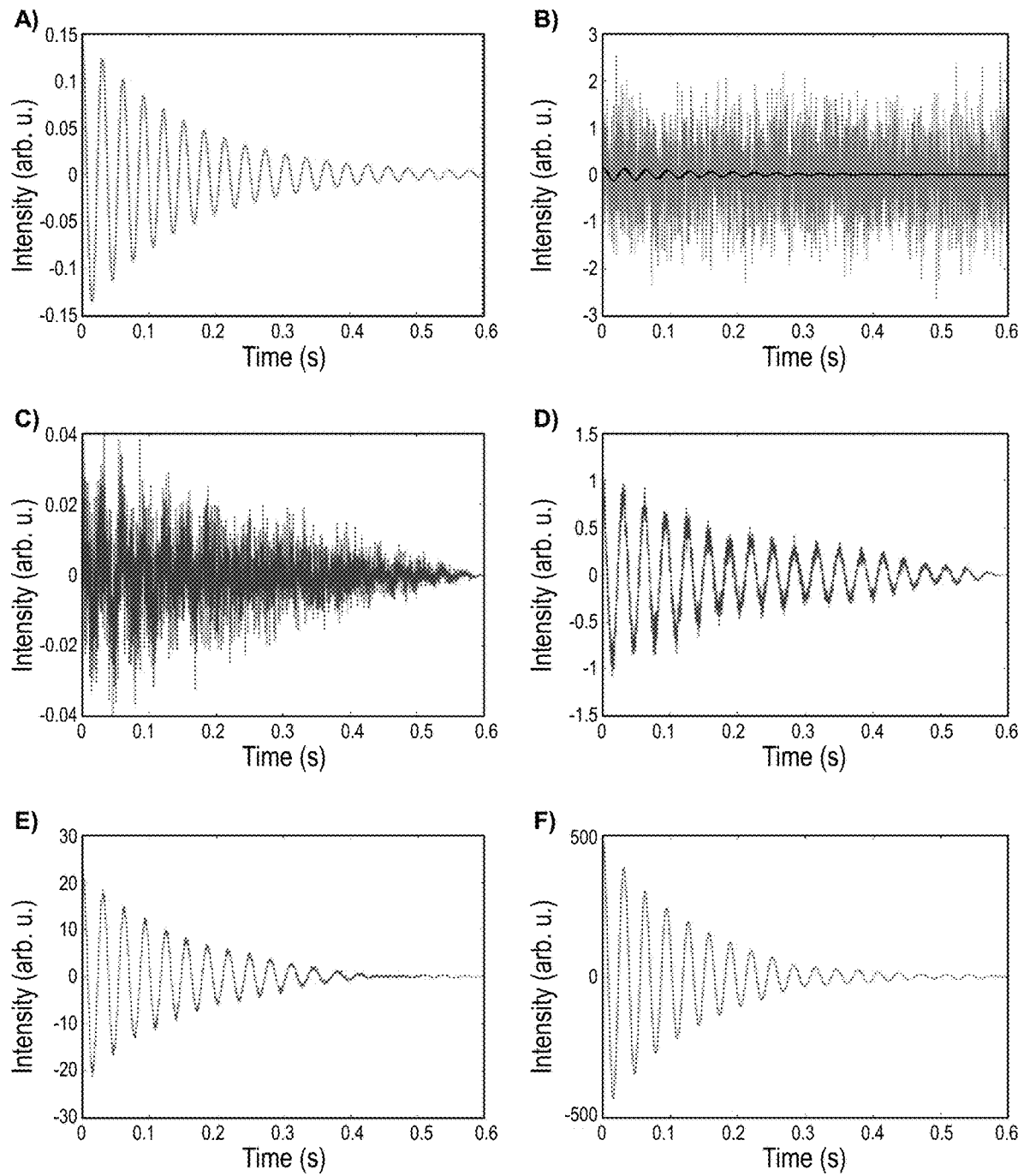
FIG. 11 is a second illustrative example of the method, depicting the effect of different numbers of initial FIDs with RECREATE using 2-cross-correlation. The initial SNR of the noisy signal is 0.15 and the number of data points per signal is 4096 A) The true FID without noise. B) The true signal with additive, white Gaussian noise with SNR=0.15. True signal overlaid in red to show scale. C) The recovered signal with 4 initial FIDs. D) The recovered signal with 8 initial FIDs. E) The recovered signal with 16 initial FIDs. F) The recovered signal with 32 initial FIDs.
Figure 12:
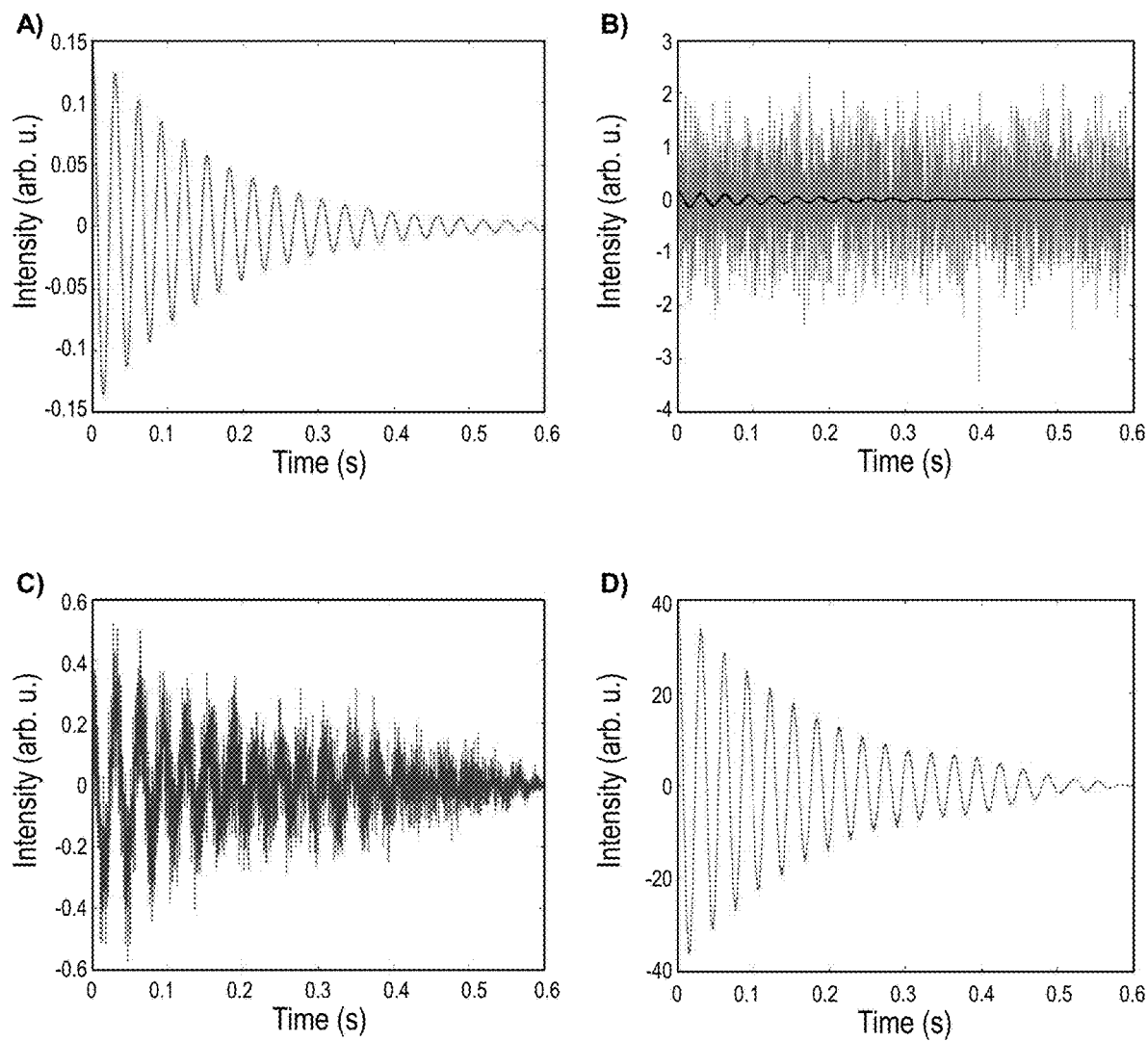
FIG. 12 is a third illustrative example of the method, depicting the effect of number of cross-correlations with RECREATE using 16 initial FIDs. The initial SNR of the noisy signal is 0.15 and the number of data points per signal is 4096 A) The true FID without noise. B) The true signal with additive, white Gaussian noise with SNR=0.15. True signal overlaid in red to show scale. C) The recovered signal with 1-cross-correlation RECREATE. D) The recovered signal with 2-cross-correlation RECREATE.
Figure 13:
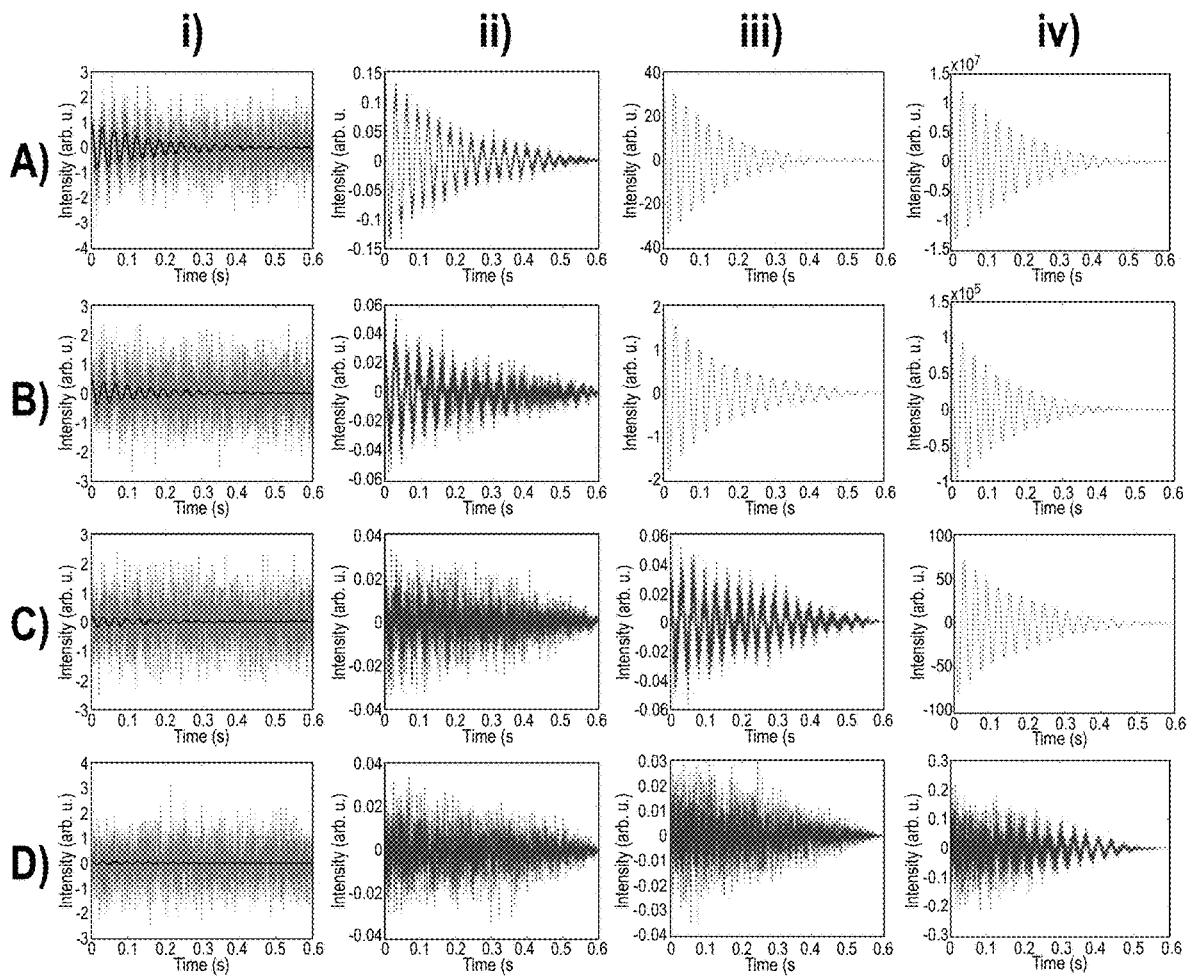
FIG. 13 is a fourth illustrative example of the method. The columns correspond to different numbers of d-cross-correlation used for the RECREATE algorithm. The rows correspond to Various initial SNR FIDs with true signal overlaid in red (i), 1-cross-correlation with 2 initial FIDs (ii), 2-cross-correlation with 4 initial FIDs (iii), 3-cross-correlation with 8 initial FIDs (iv). The number of initial FIDs were chosen to be the minimum required for each d-cross-correlation. The initial SNRs in rows A) SNR=1, B) SNR=0.5, C) SNR=0.2 and D) SNR=0.08.
Figures 15, 16:
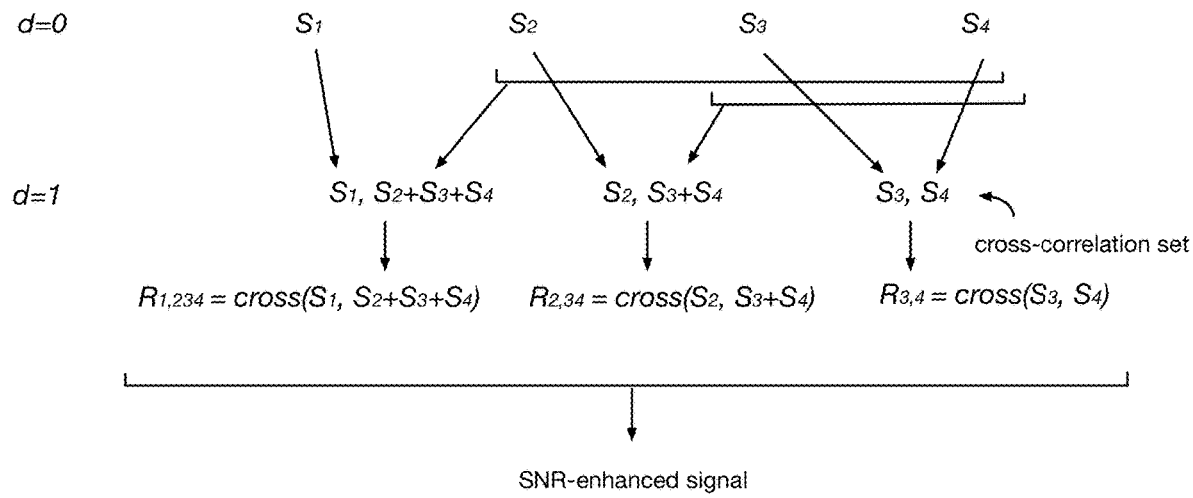
FIG. 15 is an illustrative example of cross-correlation sets, in variants.
FIG. 16 is an example of the number of unique cross-correlation steps for a given number of initial data sets (m), in variants.

As shown in FIG. 2, recursively cross-correlating the unique measurements can include: optionally determining a number of iterations (d) S210; optionally determining cross-correlation sets S230; and cross-correlating the signals within the cross-correlation sets S250 for d iterations (illustrative examples shown in FIG. 9 and FIG. 15). However, S250 can be otherwise performed.

Determining a number of iterations (d) S210 functions to determine the number of recursion loops to use, where the number of recursion loops contributes to the number of unique cross-correlation outputs (N) used to determine the denoised signal in S300. The number of iterations (d) can be: predetermined, selected, calculated, looked up (e.g., from a lookup table), iteratively determined, randomly determined, determined using an optimization, or otherwise determined. The number of iterations (d) can be determined based on: the SNR of one or more measurements in the set (e.g., wherein a higher d can be used when the signal measurements have an initial SNR below a SNR threshold); a desired N (e.g., determined based on the SNR, predetermined, etc.); available computational power; desired computation speed (e.g., determined based on the use case or disease state); the signal source parameters (e.g., anticipated concentration, anticipated signal strength, etc.); a combination thereof; and/or another parameter. S210 can be performed: for every method instance; in response to the maximum N exceeding a predetermined threshold (e.g., determined based on the number of signal measurements m); once; and/or at any other suitable time.

In a first example, S210 includes: setting d to a predetermined number. Examples of d can include: 1, 2, 3, 4, 5, 10, 20, 30, 100, between 1 and 100, at least 1, at least 2, more than 100, and/or any other suitable number.

In a second example, d (e.g., maximum d) can be determined using:

$$N_d(m_{FID}) = \frac{1}{2^{2^d-1}} P(m_{FID}, 2^d) = \frac{1}{2^{2^d-1}} \frac{m_{FID}!}{(m_{FID} - 2^d)!},$$

where $$P(m_{FID}, 2^d) = \frac{m_{FID}!}{(m_{FID} - 2^d)!},$$

where $m_{FID}$ is the number of initial measurements (e.g., FIDs), $N_d$ is the number of unique cross-correlation outputs, and d is the number of iterations.

In a third example, S210 includes: determining an initial SNR from a signal measurement; determining a number of unique cross-correlation outputs N based on the initial SNR (higher N for lower SNR); and determining the number of iterations d based on N (e.g., using the second example discussed above). The number of cross-correlation outputs N can be determined by: calculating N based on the initial SNR; calculating N based on the initial SNR and a predetermined, desired, or target improvement ($\sqrt{N}$); looking up N based on the initial SNR; and/or otherwise determining the number of cross-correlation outputs N.

In a fourth example, S210 includes iteratively determining d by: selecting an initial number of iterations $d_1$ (e.g., 2), determining the SNR-enhanced signal using $d_1$, evaluating the SNR-enhanced signal for an analyte of interest, and if the analyte is not detected or recognized, increasing the number of iterations and repeating the method.

In a fifth example, S210 includes calculating d (e.g., the maximum possible d) using: $d = \lfloor \log 2(m) \rfloor$, where $\lfloor \ \rfloor$ is the floor function.

In a sixth example, S210 includes determining d based on the computational resources available to the method, such as the amount of available processing power (e.g., number of threads, % CPU, etc.), the amount of available memory, amount of available energy, amount of disc space, and/or other computational resources. d can be selected from a lookup table, calculated, or otherwise determined.

In a seventh example, S210 includes determining d using a multifactorial optimization. The factors can include: a desired analyte parameter accuracy; the SNR of the measurement(s); the available computing resources; and/or any other factor.

In an eighth example, S210 includes determining a target improvement ($\sqrt{N}$); determining the number of cross-correlation outputs N needed to achieve the target improvement; and determining the number of iterations d needed to obtain N, given the number of measurements m. The target improvement can be determined based on the initial SNR, be a predetermined value, and/or be otherwise determined.

However, d can be otherwise determined.

Determining cross-correlation sets S230 functions to reduce the number of cross-correlations that are calculated, which reduces the total number of cross-correlation outputs (C) (e.g., unique d-cross-correlation outputs) that are computed, which, in turn, can decrease computational time and resources. This can be advantageous when computing power is limited (e.g., to a user device, a wearable's computing system, a microprocessor, etc.), because higher m and d values causes C to grow factorially (example shown in FIG. 14), which can result in compute times possibly exceeding the useful response time and/or the compute requirements exceeding the available resources.

A cross-correlation set (CCS) preferably includes the elements that will be cross-correlated in the iterations. Each cross correlation set can include two or more elements (e.g., include a pair of elements ($e_i$, $e_j$), 3, 4, 5, or any other suitable number of elements), but can alternatively have less than two elements.

The elements ($e_i$) are preferably signals, but can alternatively be summed signals or other data structures. The elements ($e_i$) can be signal measurements ($S_i$) (e.g., determined in S100), previously-determined cross-correlation outputs ($R_{ij}$) (e.g., from a prior S200 iteration), or other elements. The elements within a cross-correlation set are preferably from the same iteration or cycle (e.g., same d), but can alternatively be from different iterations. However, a cross-correlation set can be otherwise defined.

The elements of the cross correlation set (e.g., the signal measurements or previously-determined cross-correlation outputs) are preferably unique, both within the set and within the set of cross-correlation sets, to prevent auto-correlations (e.g., such that the CCS includes a set of unique measurements). Unique elements can be: unique measurements; elements generated from disparate constituent or underlying elements (e.g., cross-correlation outputs generated from different signal measurements); uncorrelated elements; and/or otherwise defined. For example, the cross-correlation output ($R_{ij}$) of a cross-correlation between a first and second element ($e_i$, $e_j$) can be treated as representative of the first and second elements ($e_i$, $e_j$) for autocorrelation purposes when selecting elements for inclusion in a cross-correlation set, such that the cross-correlation output ($R_{ij}$) is not included in a cross-correlation set that has cross-correlation outputs that were also generated from $e_i$ or $e_j$. However, the elements within a cross-correlation set can alternatively be nonunique (e.g., share a signal measurement with another element, such that the elements can be autocorrelated) or otherwise related.

The cross correlation sets can be: predetermined, retrieved, selected, and/or otherwise determined.

Each instance of S230 can determine: a single cross-correlation set, multiple cross-correlation sets, and/or any number of cross-correlation sets. Each cross-correlation set (CCS) within the resultant set of cross-correlation sets (set of CCSs) preferably represents a unique measurement combination permutation within the resultant set (e.g., the CSSs are unique sets), but can alternatively be nonunique. Each cross-correlation set within the resultant set can have the same or different number of elements. When the resultant set of CCSs is split into iterations or epochs, the CCSs within the same epoch can have the same or different number of elements.

The set of cross-correlation sets preferably includes enough CCSs to generate N cross-correlation outputs by iteration d, but can alternatively include any other suitable number of pairs. Elements can be selected for inclusion within a CCS: randomly, based on an optimization, according to a rule or heuristic (e.g., selecting the CCSs corresponding to a predetermined set of matrix indices from a permutation matrix listing all unique element pairs), or otherwise selected. When more CCSs (e.g., unique measurement combination permutations) are available than needed to achieve N cross-correlation outputs, the CCSs can be selected for inclusion in the analysis set: randomly, based on an optimization, according to a rule or heuristic, or otherwise selected. Alternatively, all cross-correlation pairs can be used.

The sets of cross-correlation sets can be: predetermined, dynamically determined (e.g., during runtime), or otherwise determined. S230 can be performed before all iterations of S250, after each iteration of S250, or performed at any other suitable time.

In a first variant, the elements to include in each CCS are selected according to a predetermined matrix. The matrix can define which element combinations to combine for each iteration or epoch.

In a second variant, the elements to include in each CCS can be randomly selected, wherein the combination of elements in the CCS can be checked for autocorrelations, retained when no autocorrelations are encountered, and discarded or modified (e.g., by selecting another element) when autocorrelations are encountered.

In a third variant, the elements in each CCS can include a primary signal (e.g., primary signal for cross-correlation purposes) and a sum of the remaining signals. This can be particularly useful when d=1, or for other values of d. The remaining signals can be all other signals that have not been used as primary signals for other CCSs, all other signals above an index of the primary signal (e.g., for primary signal s, all signals having an identifier above s; all signals that are delayed relative to the primary signal), all other signals (e.g., determined in S100), a set of randomly selected signals, and/or other signals. For example, for m signals, a first CCS can include the first signal and a sum of signals 2 to m, a second CCS can include the second signal and a sum of signals 3 to m, and so on (illustrative example shown in FIG. 15). This can result in m−1 cross-correlation steps (e.g., example values shown in FIG. 16), which can increase the processing speed of the evaluation (e.g., when m is 4 or more).

However, the set of CCSs can be otherwise determined.

Cross-correlating the cross-correlation sets S250 functions to iteratively remove uncorrelated noise by recursively cross-correlating unrelated measurements (and derivative output functions) of the same signal source. S250 is preferably repeated for d iterations, using different CCSs from the set of CCSs, but can be repeated any number of times, using any CCS.

Cross-correlating the cross-correlation sets preferably includes cross-correlating the elements (e.g., signals) within each cross-correlation set, but can additionally or alternatively include cross-correlating different CCSs together, or otherwise cross-correlating the elements or sets thereof. The elements within each set can be cross-correlated in a predetermined order, in a random order, in a reversed order, or in any other suitable order. The predetermined order can be: in order of earliest signal to latest signal (or vice versa) (e.g., earlier signal first, then delayed signal second), in order of highest SNR to lowest SNR (or vice versa), based on an index or identifier value assigned to the signal, or any other suitable order.

Figure 7:
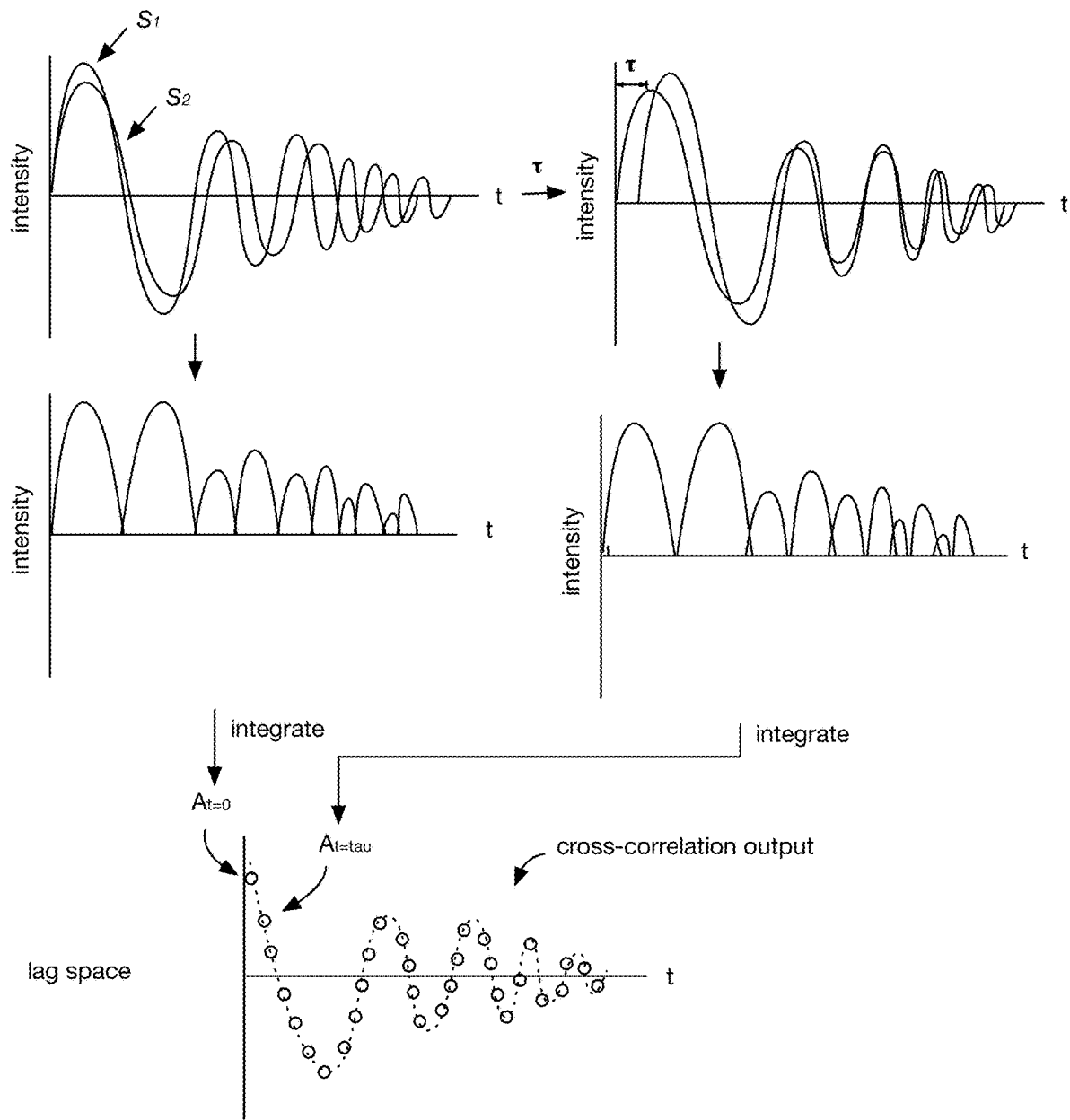
FIG. 7 is an illustrative example of cross-correlating a first and second signal.

Cross-correlating the selected cross-correlation sets preferably includes displacing one element (of the cross-correlation set) relative to the other (e.g., using a sliding dot product or sliding inner product) and calculating the cross-correlation output in lag space (example shown in FIG. 7), but can be otherwise performed.

In an example, the cross correlation of a first and second signal measurement can be calculated as:

$$R_{12} = \text{cross}(S_1, S_2) = R_{S_1 S_2}(\tau) = \int_{t_i}^{t_e} S_1(t) \overline{S_2(t+\tau)} dt$$

where $R_{S_1 S_2}$ is the cross-correlation output, $S_1$ is the first signal measurement, $S_2$ is the second signal measurement, $\tau$ is the lag, t is time, and the overline denotes the complex conjugate.

In a first variant, $t_i$ is the time at which signal acquisition begins ($t_i=0$), and $t_e$ is the time at which signal acquisition ends ($t_{acq}$). In this variant, the second signal is slid in the positive time direction relative to the first signal.

In a second variant, $t_i$ can be the inverse of $t_e$ ($t_i=-t_{acq}$), and $t_e$ is the time at which signal acquisition ends ($t_{acq}$). In this variant, the second signal is slid in both the positive and negative time directions relative to the first signal, resulting in a signal centered around $t=_0$. In this variant, the negative portion of the signal can be optionally inverted and summed with the positive portion of the signal (e.g., before a subsequent cross-correlation iteration). In variants where the negative portion is inverted, the resultant frequency peak can be inverted (in the frequency domain, after S400). However, the resultant signal can be otherwise processed.

In one example, $S_1$ and $S_2$ have the form:

$$S_x(t) = a_x e^{-t/T_2} e^{i\omega t} + n_x \mu_x(t)$$

where x is the signal measurement identifier, $a_x$ is the signal amplitude from the measurement, $\mu_x(t)$ is the Gaussian noise function for the measurement, and $n_x$ is the noise amplitude (e.g., peak-to-peak noise). This specific example assumes that the noise in the measurements are (largely) uncorrelated.

Figure 8:
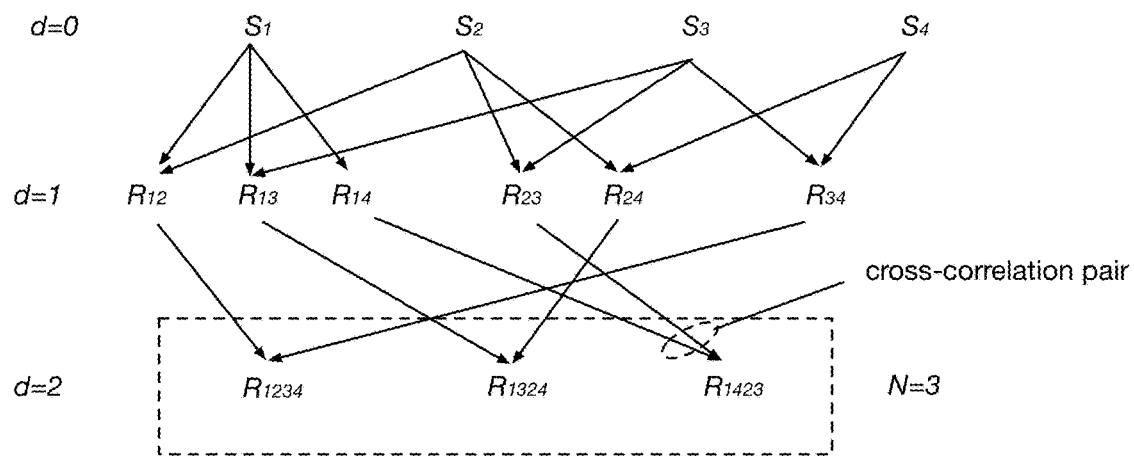
FIG. 8 is an illustrative example of recursively cross-correlating the unique measurements.

Performing the cross-correlation for d iterations uses the outputs from the prior iteration as the inputs for the next iteration, wherein the output element (e.g., the generated signal) is used as an element within the next cross-correlation set (example shown in FIG. 8).

In particular, in subsequent cross-correlation iterations (e.g., $1 < i \leq d$), $S_1$ and $S_2$ can be replaced with the outputs of the prior cross-correlation iteration (i−1) (e.g., the elements of the subsequent cross-correlation pairs, such as ($R_{12}$, $R_{34}$), respectively; ($R_{1234}$, $R_{5678}$), respectively; etc.). The cross-correlation outputs are iteratively cross-correlated themselves until d iterations have been satisfied. However, the cross-correlation can be otherwise performed for d iterations.

In an illustrative example, the cross-correlation outputs for a set of m=4 signals include: $R_{12}$=cross ($S_1$, $S_2$), $R_{23}$=cross ($S_2$, $S_3$), $R_{34}$=cross ($S_3$, $S_4$), $R_{14}$=cross ($S_1$, $S_4$), $R_{13}$=cross ($S_1$, $S_3$), $R_{24}$=cross ($S_2$, $S_4$), $R_{1234}$=cross ($R_{12}$, $R_{34}$), $R_{1324}$=cross ($R_{13}$, $R_{24}$), and $R_{1423}$=cross ($R_{14}$, $R_{23}$). An example is shown in FIG. 8.

In an illustrative example (shown in FIG. 8), for m=4 and d=2, S250 can include calculating: $R_{12}$, $R_{34}$, $R_{14}$, $R_{23}$, $R_{24}$, and $R_{13}$ in the first iteration (d=1), and $R_{1234}$, $R_{1324}$, and $R_{1423}$ in the second iteration (d=2).

However, the selected cross-correlation pairs can be otherwise cross-correlated for d iterations.

Figure 3:
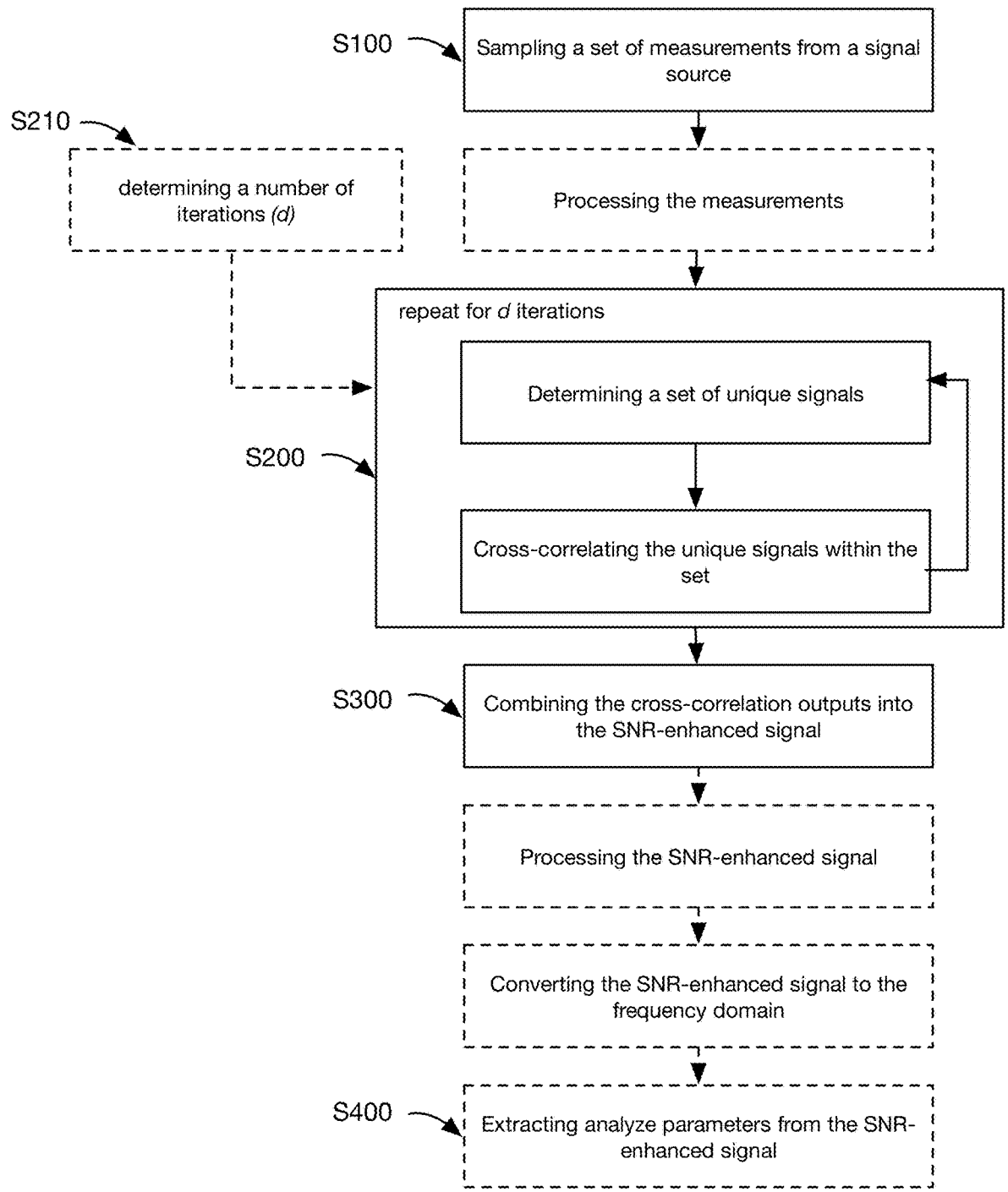
FIG. 3 is a flowchart diagram of an illustrative example of the method.

In an illustrative example (example shown in FIG. 3), S200 includes recursively, for d iterations: determining a set of unique signals (e.g., non-autocorrelated signals) and cross correlating the signals within the set, wherein the output of the cross-correlation is used as a signal within the set for the next iteration. The output of the cross-correlation can also be treated as representative of the constituent signals (e.g., within the set of unique signals used to generate the output) for autocorrelation determination purposes. In this example, d can be predetermined (e.g., set to 1, 2, 3, 4, or any number). In this example, the unique signal sets for each iteration can be predetermined (e.g., the permutations of signal combinations are predetermined). However, S200 can be otherwise performed.

Determining a SNR-enhanced signal from the cross-correlation outputs S300 functions to output a final signal for analyte parameter analysis. The SNR-enhanced signal preferably has noise reduced relative to the unique measurement(s), but can be otherwise characterized.

The SNR-enhanced signal is preferably generated from all or a subset of the cross-correlation outputs from the last cross-correlation iteration (e.g., the last step of cross-correlations; the $d^{th}$ round of cross-correlations), but can additionally or alternatively be generated from intermediary cross-correlation outputs (e.g., output by intermediary cross-correlation iterations), the signal measurements, and/or other elements.

S300 preferably includes summing the cross-correlation outputs to generate the SNR-enhanced signal (e.g., possible because all the cross-correlation outputs are in the same functional form as the signal measurements), but can additionally or alternatively include averaging, multiplying, subtracting, dividing, and/or otherwise processing the cross-correlation outputs to generate the SNR-enhanced signal.

The SNR-enhanced signal is preferably generated from N elements (e.g., signals, cross correlation outputs, signal measurements, etc.), but can additionally or alternatively be generated from more or less elements. N is preferably be the number of cross-correlations output by the last cross-correlation iteration (e.g., the last step of cross-correlations; the $d^{th}$ round of cross-correlations). In the illustrative example above for m=4 and d=2, N=3 (example shown in FIG. 8). In the illustrative example, S300 would include summing $R_{1234}$, $R_{1324}$, and $R_{1423}$ to obtain the SNR-enhanced signal. However, N can alternatively be the number of all cross-correlation outputs generated from the signal measurements (C) (e.g., inclusive of all intervening cross-correlation outputs output by all iterations; the number of uniquely defined d-cross correlations; etc.), example shown in FIG. 14; be the number of all intermediary cross-correlation outputs that were generated in addition to the number of signal measurements (C); be less than the number of cross-correlations output by the last cross-correlation iteration; or be otherwise defined. N can be a result of the number of measurements (m) and iterations (d), be a predetermined number (e.g., 1, 2, 3, 4, 5, 8, 10, 13, 16, 32, 64, etc.), and/or be otherwise determined.

The method can optionally include processing the SNR-enhanced signal, which can improve the spectral resolution in the frequency domain. The SNR-enhanced signal is preferably processed in the time domain, but can alternatively be processed in the frequency domain or other domain. Processing the SNR-enhanced signal can include: zero-filling the signal; line broadening; baseline correction; altering the phasing; defining integration regions; distortion correction; smoothing; decimating; gaussian mixture modelling; and/or otherwise processing the SNR-enhanced signal.

Determining an analyte parameter based on the SNR-enhanced signal S400 functions to characterize the analyte within the sample. The analyte parameter can be presented to a user (e.g., on a user device), provided to a downstream process for subsequent analysis (e.g., exercise recommendations, diet recommendations, medication recommendations, treatment recommendations, etc.), be logged in a timeseries, and/or otherwise used. Examples of the analyte parameter include: quantitative measurements, qualitative measurements, relative concentration, absolute concentration, molar concentration, number of moles, mass, purity, analyte identity, molecular structure elucidation, analyte dynamics, analyte reaction state, sampling environment (e.g., chemical environment), sampling environment interactions, and/or any other suitable parameter. S300 can include: transforming the SNR-enhanced signal to the frequency domain (e.g., extracting the frequency-domain spectrum using a Fourier transform); and extracting the analyte parameter from the SNR-enhanced signal in the frequency domain using NMR techniques (e.g., peak integration).

An alternative embodiment implements the above methods and/or processing modules in non-transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A system, comprising:
    a nuclear magnetic resonance (NMR) device, configured to sample a plurality of signals from a target analyte; and
    a processing system, configured to:
        generate cross-correlation outputs by recursively cross-correlating signals within unique sets of signals, wherein each unique set of signals comprises at least two distinct signals with non-overlapping datapoints from the plurality of signals; and
        determine a parameter of the target analyte based on the cross-correlation outputs.

2. The system of claim 1, wherein the unique sets of at least two distinct signals comprise unique combinations, without repetition, of signals from the plurality of signals.

3. The system of claim 2, wherein the unique sets of at least two distinct signals for a subsequent iteration comprise unique combinations of signals selected from cross-correlation outputs of a prior iteration.

4. The system of claim 1, wherein the NMR device comprises a wearable housing comprising a bore, wherein the bore defines a measurement volume, wherein the plurality of signals are sampled from the measurement volume, and wherein a portion of the measurement volume is configured to receive a human appendage.

5. The system of claim 4, wherein the human appendage is a finger.

6. The system of claim 4, wherein the target analyte comprises an in-situ analyte within the human appendage, wherein the parameter comprises a concentration of the analyte.

7. The system of claim 6, wherein the analyte comprises glucose.

8. The system of claim 1, wherein each of the at least two distinct signals is not autocorrelated.

9. The system of claim 1, wherein the plurality of signals comprises subsignals subsampled from a parent nuclear magnetic resonance (NMR) signal.

10. The system of claim 1, wherein the processing system is configured to determine the parameter of the target analyte based on aggregated cross-correlation outputs.

11. The system of claim 10, wherein the aggregated cross-correlation outputs collectively form a signal-to-noise ratio (SNR)-enhanced signal, wherein the processing system is configured to transform the SNR-enhanced signal to a frequency domain and determine the parameter based on the transformed SNR-enhanced signal.

12. A method, comprising:
    determining a plurality of signals associated with an analysis a target analyte;
    generating cross-correlation outputs by, for at least a first iteration, cross-correlating a set of signals within unique subsets of signals, wherein each unique subset of signals comprises at least two distinct signals determined from the plurality of signals;
    determining a processed signal based on cross-correlation outputs; and
    determining parameters of the target analyte based on the processed signal.

13. The method of claim 12, wherein the unique subsets of at least two distinct signals comprise unique combinations, without repetition, of signals determined from the plurality of signals.

14. The method of claim 13, wherein the unique subsets of at least two distinct signals for a subsequent iteration comprise unique combinations of signals selected from cross-correlation outputs of a prior iteration.

15. The method of claim 12, wherein the target analyte comprises an in-situ analyte within a human body, wherein the parameter comprises a concentration of the analyte.

16. The method of claim 12, wherein the cross-correlation outputs are in lag-space.

17. The method of claim 12, wherein each of the at least two distinct signals is not autocorrelated.

18. The method of claim 12, wherein the plurality of signals are subsignals subsampled from a parent nuclear magnetic resonance (NMR) signal.

19. The method of claim 12, wherein each unique subset of at least two distinct signals comprises a primary signal and a sum of all signals from the plurality of signals that are delayed relative to the primary signal.

20. The method of claim 12, wherein determining the processed signal comprises aggregating the cross-correlation outputs, wherein the processed signal comprises a signal-to-noise ratio (SNR)-enhanced signal.

* * * * *